(12) United States Patent
Ericsson

(10) Patent No.: US 10,533,150 B1
(45) Date of Patent: Jan. 14, 2020

(54) ELECTROMAGNETIC BIOSTIMULATION APPARATUS AND METHOD

(71) Applicant: John Drew Ericsson, Gulf Breeze, FL (US)

(72) Inventor: John Drew Ericsson, Gulf Breeze, FL (US)

(*) Notice: Subject to any disclaimer, the term of this patent is extended or adjusted under 35 U.S.C. 154(b) by 0 days.

(21) Appl. No.: 16/182,778

(22) Filed: Nov. 7, 2018

Related U.S. Application Data

(60) Provisional application No. 62/582,491, filed on Nov. 7, 2017.

(51) Int. Cl.
| | |
|---|---|
| *C12M 1/42* | (2006.01) |
| *C12M 1/34* | (2006.01) |
| *C12M 1/00* | (2006.01) |
| *C12M 3/00* | (2006.01) |

(52) U.S. Cl.
CPC ............ *C12M 31/10* (2013.01); *C12M 21/08* (2013.01); *C12M 35/02* (2013.01); *C12M 41/36* (2013.01); *C12M 41/46* (2013.01)

(58) Field of Classification Search
CPC ...... C12M 35/02; C12M 35/04; C12M 35/06; C12M 31/01; C12M 31/12; C12M 41/14; C12M 41/36; C12M 41/48
See application file for complete search history.

(56) References Cited

U.S. PATENT DOCUMENTS

| | | | | |
|---|---|---|---|---|
| 4,952,511 A | * | 8/1990 | Radmer | ................. C12M 21/02 362/340 |
| 8,569,050 B1 | * | 10/2013 | Ericsson | ................. C12N 1/12 435/292.1 |
| 10,059,917 B2 | * | 8/2018 | Kim | ......................... C12M 1/34 |

* cited by examiner

*Primary Examiner* — William H. Beisner
(74) *Attorney, Agent, or Firm* — J. Nevin Shaffer, Jr.

(57) ABSTRACT

An electromagnetic biostimulation apparatus and method includes a container with an outer wall, a bottom, and a top such that an open interior space is formed. Several biotubes are located within the container and an energy transmission device is provided where the energy transmission device is directed at less than all of the several biotubes. A laser beam and optical density reader device combination is provided where the optical density reader device obtains data from the laser beam related to each of the several biotubes.

8 Claims, 10 Drawing Sheets

ELECTROMAGNETIC BIOSTIMULATION APPARATUS AND METHOD

CROSS REFERENCE TO RELATED APPLICATION

This application claims the benefit of previously filed U.S. provisional patent application No. 62/582,491 filed Nov. 7, 2017 for "The 'BioStim' electromagnetic energy-biostimulation research system". The Applicant hereby claims the benefit of this provisional application under 35 U.S.C. § 119. The entire content of this provisional application is incorporated herein by this reference.

FIELD OF THE INVENTION

This invention relates to an electromagnetic biostimulation research device. In particular, in accordance with one embodiment, the invention relates to an electromagnetic biostimulation research device including a container with an outer wall, a bottom, and a top such that an open interior space is formed. Several biotubes are located within the container and an energy transmission device is provided where the energy transmission device is directed at less than all of the several biotubes. A laser beam and optical density reader device combination is provided where the optical density reader (ODR) device obtains data from the laser beam related to each of the several biotubes. In a preferred embodiment, the ODR obtains positive or negative growth (darker to lighter organism concentration) data related to each of the several biotubes and with special computer software data analysis of the stimulation results and notifies via email the attending researcher of the positive-negative growth events for further analysis. The present invention may also contain an AUTO sampling system that programs the periodic extraction of fluids via micro-tubing fluid lines connected to each biotube containing the organism of interest into a fluid particle imaging and analysis system (Fluid Imaging Technology—FlowCam) for viewing and further analyzing the cell growth rate and characteristics of each organism in each biotube.

BACKGROUND OF THE INVENTION

A problem exists in the field of biological research with regard to the determination of the positive and negative growth effects when various forms of electromagnetic energy are applied upon microorganisms that are produced to create food nutrient's like Omega 3 oils, biofuels, yeast in food, alcohol and related beverages, valuable cosmetic compounds, nutraceuticals like Astaxanthin antioxidant, and pharmaceutical products created for the treatment of various illnesses and for speeding up the production rate of inoculation drugs for influenza outbreaks. It is known that some forms of electromagnetic energy enhance organism growth rates dramatically by over three hundred percent per day while other forms of electromagnetic energy can inhibit growth. Which types and amounts of electromagnetic energy works with various types of these microorganisms is a puzzle worth solving as mankind's growing needs for these products expand with the worlds population.

Previous research efforts on the "cause and effect" of low-level electromagnetic field (EMF) energy exposure on all manner of living organisms was initiated in the 1950's as a result of Russian and USA space flight and exploration programs. Very few of the prior research methods and systems were described in publications sufficient to replicate the electromagnetic biostimulation research system used nor was the methodology or results of these early EMF research efforts made clear and reproducible.

Applicant's U.S. Pat. No. 8,569,050 describing a commercial scale, enclosed bioreactor system discloses that it contains an electromagnetic biostimulation component located in the upper dome of the bioreactor and in the recirculation system that increases biomass growth rate in some algae up to three hundred percent. The prior art includes others that have confirmed a connection between the application of electromagnetic biostimulation energy on the growth rate of some organisms. What is missing in the art and what is required to fill a long felt need in the biotechnology industry is a device to determine the accurate and discrete application of a variety of energy forms on a range of organisms including a control group of organisms such that the cause and effect of a particular form of energy on a particular organism is determinable.

Thus, there is a need in the art for an electromagnetic biostimulation device that provides for the controlled application of selectable forms of energy on selected organisms and not on other organisms such that a control group is used in evaluation of the results of the biostimuation process. Further, there is a need for an electromagnetic biostimulation device that is simple to operate, compact and portable and economical in operation that can standardize the mythology and systems used in this new field of biotechnology.

It therefore is an object of this invention to provide an electromagnetic biostimulation research device that enables the controlled application of selectable forms of electromagnetic energy, including but not limited to microwave, acoustic, magnetic and other forms of EMF, on selected organisms and not on other organisms such that a control group is used in evaluation of the results of the process. Further, it is an object of the present invention to provide an electromagnetic biostimulation research device that is simple to operate, compact and portable and economical in operation.

SUMMARY OF THE INVENTION

Accordingly, the electromagnetic biostimulation apparatus and method of the present invention, according to one embodiment, includes a container with an outer wall, a bottom, and a top such that an open interior space is formed. Several biotubes are located within the container and an energy transmission device for the transmission of a selectable form of energy for biostimulation, including for example only and not by way of limitation, a microwave device, an acoustic device, a static magnetic device and a laser electromagnetic field (EMF) energy device, is provided where the energy transmission device is directed at less than all of the several biotubes. A laser beam and optical density reader device combination is provided where the optical density reader device obtains data from the level of light penetration that is transmitted by the laser beam through each of the several biotubes.

All terms used herein are given their common meaning so that "microwave device", "acoustic device", "static magnetic device", "laser generation device" and "electromagnetic field (EMF) device" identify and describe devices well known in the art and as described and illustrated herein for the transmission of a particular type of energy for use in biostimulation and are not disclosed further hereafter. Likewise, "laser beam and optical density reader device" describes a device as discussed and illustrated herein that is known in the art and not described more fully hereafter.

Further, the term "biotube" describes a tube for holding microorganisms as described and illustrated more fully hereafter and any other medium for containing test samples as is now known or hereafter developed.

In one aspect, the energy transmission device includes a microwave device, a static magnetic device, an acoustic device and a laser electromagnetic field (EMF) energy device where at least one of the microwave device, the static magnetic device, the acoustic device and the laser EMF energy device are selectively directed into the open end of less than all of the several biotubes.

Here the term "selectively" describes the ability of the present invention to enable controlled experimentation by means of the selective application of some or all energy forms to some or all of the test biotubes and not the control biotubes.

In another aspect, there are three biotubes where two biotubes are test biotubes and one biotube is a control biotube such that the energy transmission device is selectively directed at the one or two of the test biotubes and not at the one control biotube.

In one aspect, the invention further includes an LED grow light for biostimulation where the grow light is directed at all of the several biotubes.

In another aspect, the invention further includes a computer system connected with the optical density reader device where data from the several biotubes is manipulated and analyzed. In this case, the term "computer system" describes any and all electronic data manipulation and analysis devices such as a personal computer, lap top, smart phone, and the like or any other computing device now known or hereafter developed.

In one aspect, the computer analysis includes a growth rate determination and in another aspect the computer analysis includes transmission of a notice to a remote receiver of a growth rate determination above a selected amount. Here "remote receiver" includes any device electronically connected with the computer system of the invention and transmission is wireless or wired as the situation warrants without limitation.

In one aspect, the biotubes include microorganisms. As the structure of the present invention enables, a variety of substances may be examined to determine reactions to a variety of energy forms. However, in a preferred embodiment, a large number of microorganisms, such as marine and fresh water organisms, for example only, may be stimulated and analyzed in a controlled manner such that predictable treatments are determinable.

In one aspect, a microwave device includes a microwave signal generating device for the generation of a variety of microwave signals.

According to another embodiment, an electromagnetic biostimulation apparatus consists of a circular polypropylene container with an outer wall, a bottom, and a removable one-half inch thick polypropylene top with thirty-six one and one-quarter inch holes that are aligned to the 135 degree angle of the ODS laser path to the ODS reader, with a top edge such that an open interior space is formed to position the top. Several biotubes are located within the circular container top where the several biotubes include test biotubes and control biotubes. An AC powered stepper motor drives the clock wise rotating center pole and is located at the center of the circular container open interior space and extends approximately eighteen to twenty-four inches above the circular container where the rotating center pole includes a transverse support arm with a first end, a second end and a middle where the middle of the transverse support arm is connected with the rotating center pole above the circular container. A microwave device, and/or an acoustic device and/or a laser electromagnetic field (EMF) energy device are connected to the first end of the transverse support arm such that the microwave device, the acoustic device and the laser electromagnetic field (EMF) energy device rotate above at least twelve of the twenty-four test biotubes. A laser beam device is connected approximately two inches below the biotube table to the rotating center pole and an optical density reader device is connected to the second end of the transverse support arm such that the optical density reader device rotates around the outside top edge of the circular container. A two inch round plastic tube hoop contains a rare-earth magnet powered static magnetic energy device which is suspended underneath the biotube table between the inner and middle test biotube array just above where the rotating optical density laser beam which transmits to the optical density reader device which obtains data reader device related to each of the plurality of biotubes.

In one aspect, the test biotubes may be located between the rotating center pole and the control tubes in proximity to the outer wall.

In another aspect, the biotubes form three misaligned concentric rings around the rotating center pole with test biotubes in two of the misaligned concentric rings. In one aspect, there are a total of thirty-six biotubes with twelve test biotubes in two of the misaligned concentric rings and twelve control biotubes in the third misaligned concentric ring.

In a further aspect, laser beam holes are provided in the top outer edge of the circular container where the laser beam holes are configured such that a laser beam passes through each of the several biotubes as it rotates clockwise and through a laser beam hole to the optical density reader for data collection for each of the test biotubes and also each of the control biotubes.

In one aspect, a computer system is connected with the optical density reader device where data from the plurality of biotubes is manipulated and analyzed. In another aspect, computer analysis includes a bar graph displaying growth rate determination and, in a further aspect, the computer analysis includes transmission of a notice to a remote receiver of a growth rate determination above or below a selected amount.

According to another embodiment, an electromagnetic biostimulation method consists of:
a. providing a container with an outer wall, a bottom, and a top such that an open interior space is formed; several biotubes located within the container; an energy transmission device selectively directed at less than all of the biotubes; and a laser beam and optical density reader device where the optical density reader device obtains data from the laser beam related to each of the biotubes; and
b. placing microorganisms in the several biotubes and activating the energy transmission device.

In another aspect, the energy transmission device includes a microwave device, a static magnetic device, an acoustic device and a laser electromagnetic field (EMF) energy device where at least one of the microwave device, the static magnetic device, the acoustic device and the laser EMF energy device are selectively directed at less than all of the biotubes.

In one aspect, the method further includes a computer system connected with the optical density reader device where laser light penetration data from the biotubes is manipulated and analyzed, where the computer analysis includes a growth rate determination, and where the computer analysis includes transmission of a notice to a remote receiver of a growth rate determination above a selected amount.

In one aspect, the method further may also include a programmable computerized fluid sampling system connected to each biotube via micro-tubing that extracts minute quantities of liquids containing the studied microrganisms which is then systematically fed into a fluid imaging particle analyzer system (Fluid Imaging Technologies—Flow Cam analyzer) for additional in-depth study of the growth characteristics of each organism in the biostimulation research system.

DESCRIPTION OF THE DRAWINGS

Other objects, features and advantages of the present invention will become more fully apparent from the following detailed description of the preferred embodiment, the appended claims and the accompanying drawings in which:

FIG. 9 is a side close up view of two test biotubes of the invention of FIG. 1 with a static magnetic coil in between.

DETAILED DESCRIPTION OF THE INVENTION

Figure 1:
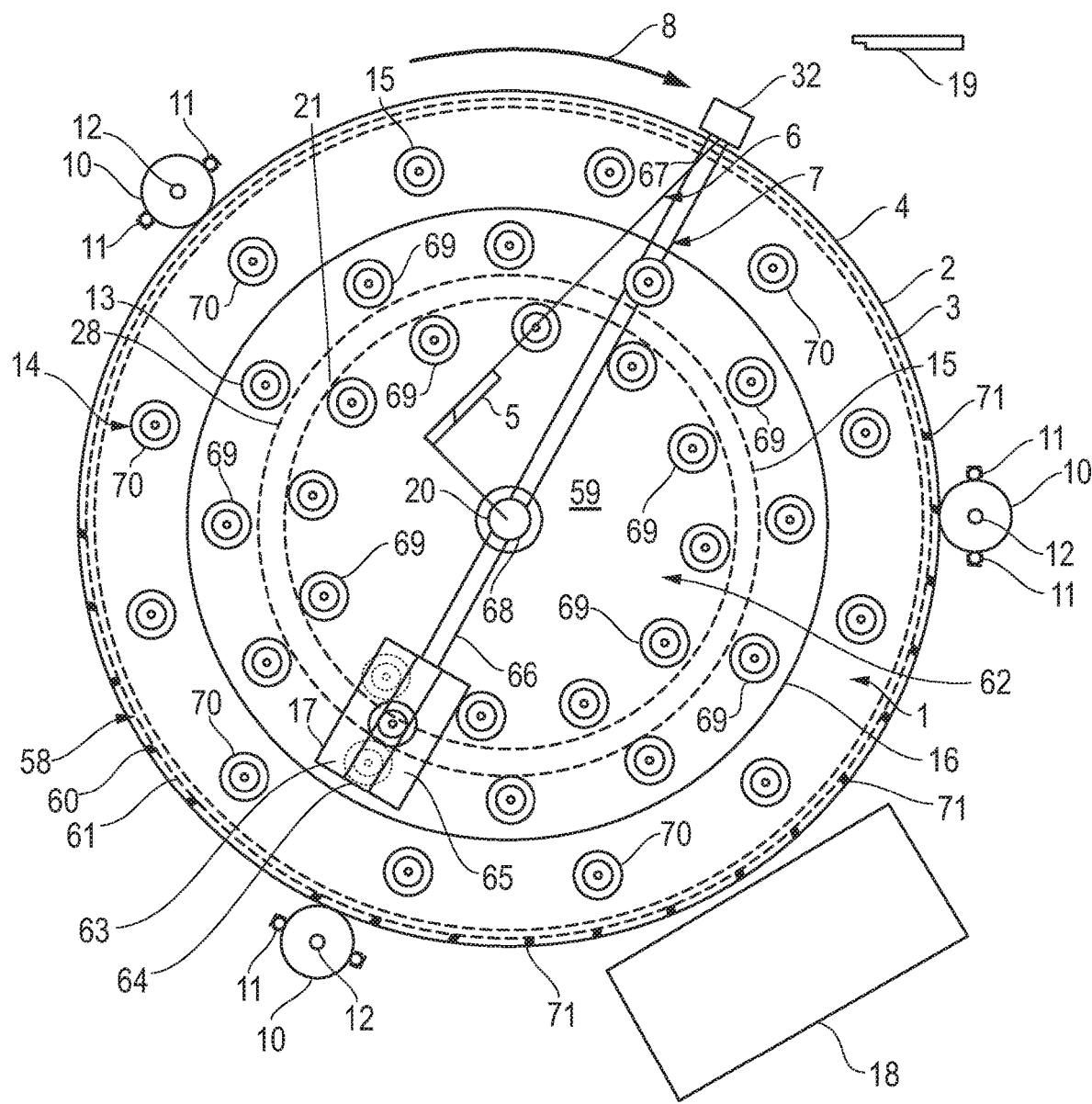
FIG. 1 is a top view of the top of the electromagnetic biostimulation apparatus of the present invention.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention.

For example, the specific sequence of the described process may be altered so that certain processes are conducted in parallel or independent, with other processes, to the extent that the processes are not dependent upon each other. Thus, the specific order of steps described herein is not to be considered implying a specific sequence of steps to perform the process. In alternative embodiments, one or more process steps may be implemented by a user assisted process and/or manually. Other alterations or modifications of the above processes are also contemplated.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

It should also be noted that a plurality of hardware and software devices, as well as a plurality of different structural components, may be utilized to implement the invention. Furthermore, and as described in subsequent paragraphs, the specific configurations illustrated in the drawings are intended to exemplify embodiments of the invention and that other alternative configurations are possible.

A preferred embodiment of the present invention is illustrated by way of example in FIGS. 1-10. Identifying numbers remain the same for the same elements in each of the Figures. With specific reference to FIGS. 1 and 2, electromagnetic biostimulation apparatus and method 1 is shown in a top view to include a container 58 with an outer wall 2, a bottom 59, and a top 60 with a top edge 61 such that an open interior space 62 is formed. Several biotubes 13 are located within the container 58 and an energy transmission device 17 is provided where the energy transmission device 17 is directed at less than all of the several biotubes 13. A laser beam 5 and optical density reader device 32 combination is provided where the optical density reader device 32 obtains data from the laser beam 5 related to each of the several biotubes 13.

According to the present invention, the energy transmission device 17 preferably includes some or all of the following: a microwave device 63, a static magnetic device 28, an acoustic device 64 and a laser electromagnetic field (EMF) energy device 65 where at least one of the microwave device 63, the static magnetic device 28, the acoustic device 64 and the laser EMF energy device 65 are selectively directed at less than all of the several biotubes 13.

Again, microwave device 63, acoustic device 64 and EMF energy device 65 are as known in the art and not described in detail and include any such devices now known or hereafter developed for the transmission of energy. Figure A shows energy transmission device 17 divided into three sections, one each for the three devices 63, 64, and 65. Certainly more devices may be included, or less, or one device used and then another substituted, all as may be most efficacious.

A clockwise rotating center pole 20 is located at the center of the circular (in a preferred embodiment) container 58 open interior space 62 and extends above the circular container 58. (More clearly shown in FIGS. 5 and 6). The rotating center pole 20 includes a transverse support arm 7 with a first end 66, a second end 67 and a middle 68 where the middle 68 of the transverse support arm 7 is connected with the rotating center pole 20 above the circular container 58. A microwave device 63, and/or an acoustic device 64 and/or a laser electromagnetic field (EMF) energy device 65 are/is connected to the first end 66 of the transverse support arm 7 such that the microwave device 63, the acoustic device 64 and the laser electromagnetic field (EMF) energy device 65 rotate above the test biotubes 13 only.

Figure 2:
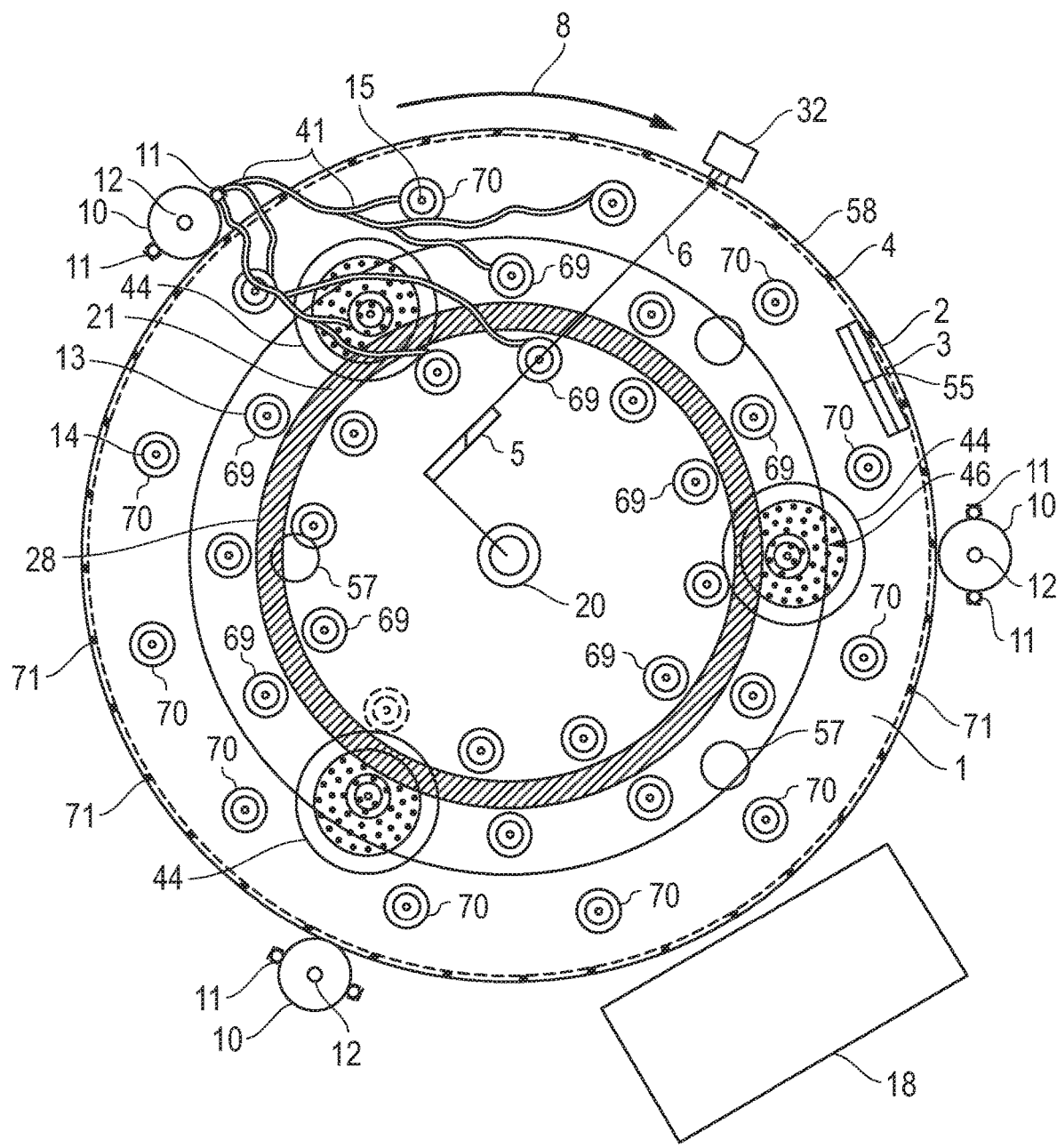
FIG. 2 is a top inside view of the invention of FIG. 1.

According to a preferred embodiment, biotubes 13 are divided into two groups: test biotubes 69 and control biotubes 70. As illustrated in FIGS. 1 and 2, preferably there are thirty six biotubes 13 consisting of 24 test biotubes 69 and twelve control biotubes 70. Certainly any number or combination of test biotubes 69 and control biotubes 70 is included within the scope of the invention. As illustrated, the biotubes 13 are formed into three misaligned concentric circles around the rotating center pole 20 and the center of container 58. As the term "misaligned" is used herein, as illustrated, from the rotating center pole 20 outward to the outer wall 2 of container 58 no two biotubes overlap. Thus, a laser beam (see beam path 6) from rotating center pole 20 to the outer wall 2 only passes through one biotube 13. Put another way, each biotube 13 is individually located to be aligned with the ODS laser and thereby accessible to a laser beam such that individual data from all biotubes 13, test biotubes 69 and control biotubes 70, is collectable as will be described more fully hereafter.

Additionally, as illustrated, the structure of the present invention, enables energy transmission device 17 to selectively direct energy down upon only the test biotubes 69, either twelve or all twenty-four of the test biotubes as desired, as it rotates around the top 60 of container 58 with the biotubes 13 below. In this manner, control biotubes 70 are unaffected by the application of tests to the test biotubes 69.

Figure 5:
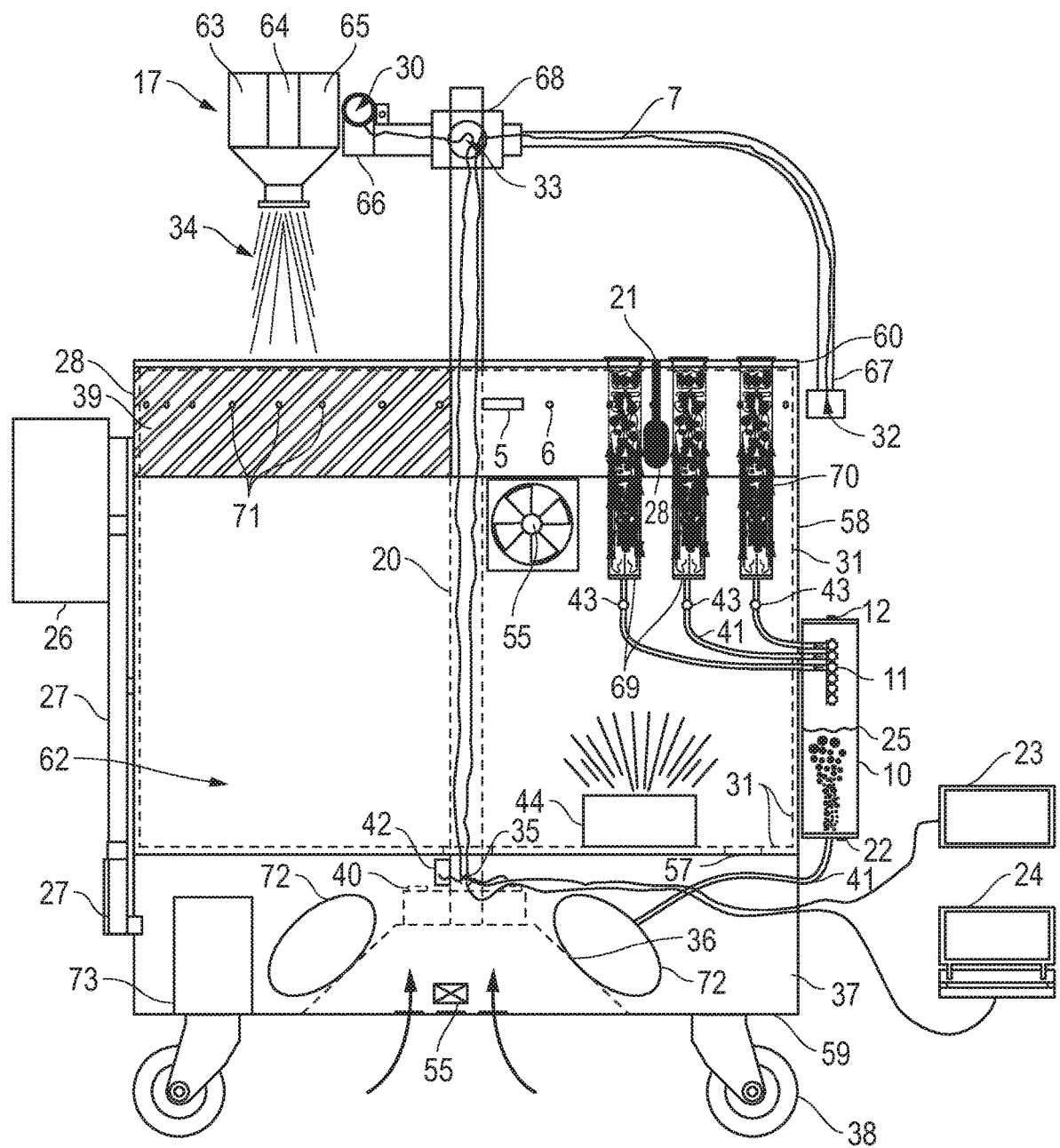
FIG. 5 is a side partial cut away view of the invention of FIG. 1.
Figure 6:
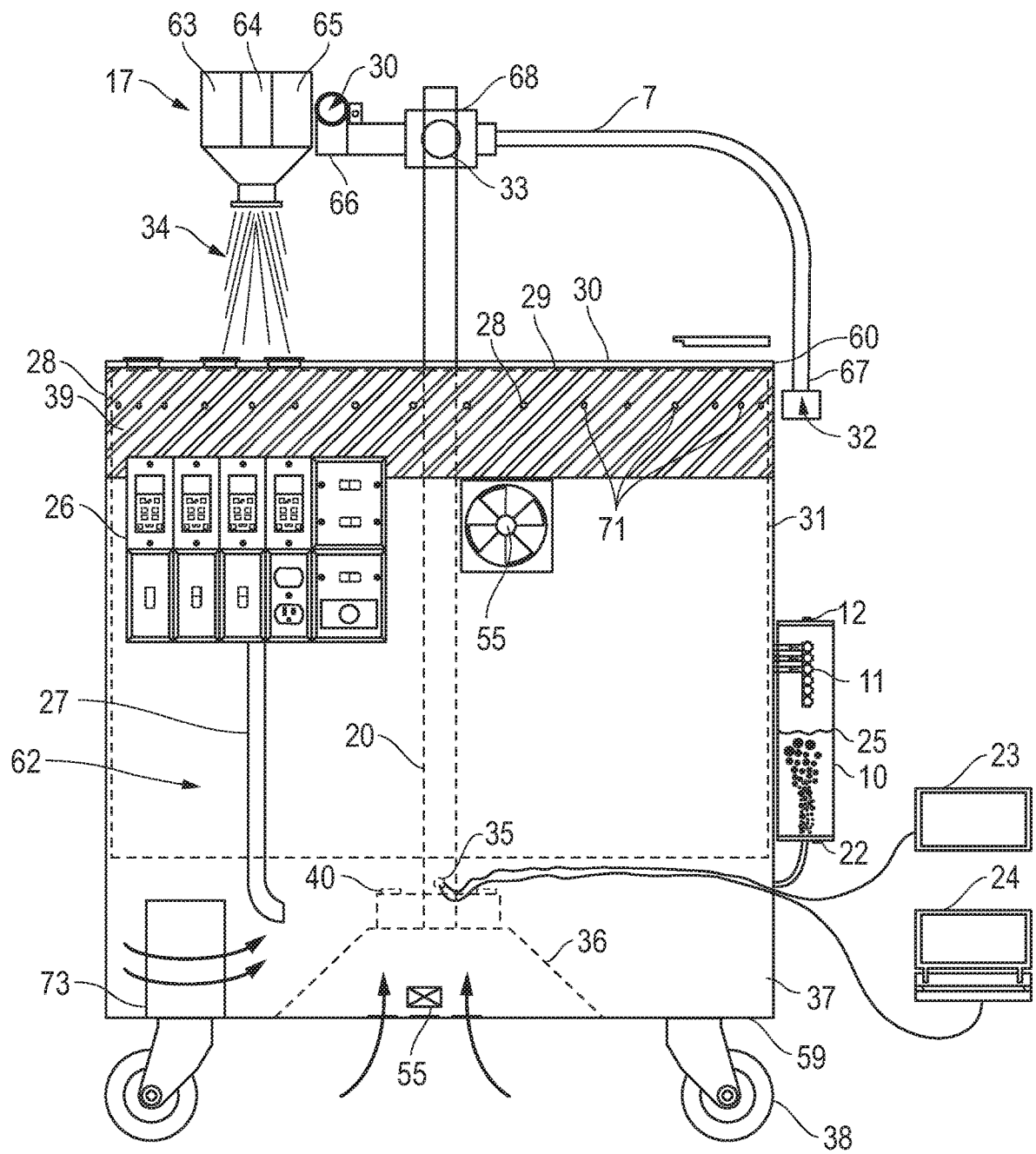
FIG. 6 is a side partial cut away view of the invention of FIG. 1 illustrating other elements.

A laser beam device 5 is connected to the rotating center pole 20 and an optical density reader device 32 is connected to the second end 67 of the transverse support arm 7 such that the optical density reader device 32 rotates around the outside of the circular container 58. Optical density reader device 32 is shown in FIGS. 5 and 6 suspended from the second end 67 below the top 60 of container 58 so as to be positioned to align with a laser beam from the laser beam device 5 that passes through the biotubes 13.

That is, laser beam device 5 is connected with rotating center pole 20 such that it is facing toward and aligned with optical density reader device 32 such that the two rotate together in a fixed spaced apart relation with all the biotubes 13 in between. In a single rotation, each of the biotubes 13 is subjected to a laser beam which passes through each biotube 13, and one and only one biotube 13 at a time, and is received by the optical density reader device 32. The laser beam includes data, such as the level of light transmitted through each tube, from which the rate of growth of an organism in the biotube 13 can be determined. In a preferred embodiment, the data is transmitted to a computer device 24 as shown in FIGS. 5 and 6, for example only.

The passage of the laser beam through the container to the optical density reader is facilitated in one embodiment by means of laser beam holes 71 in the outer edge of the circular container 58 where the laser beam holes 71 are configured such that a laser beam passes through each of the biotubes 13 as it rotates and through a laser beam hole 71 to the optical density reader 32 for data collection for each of the test biotubes 69 and each of the control biotubes 71.

According to one aspect, a static magnetic device 28 is located underneath the circular top suspending the biotubes between the inner and middle inside of the container 58 and in the proximity to the test biotubes 69. By "proximity" as shown in the illustration as at FIGS. 1, 2 and 5, the static magnetic device 28 is located in between the two groups of test biotubes 69, and preferably, between the inner misaligned concentric ring of test biotubes 69 and the next ring outward. In a preferred embodiment, top 60 of container 58 individually supports biotubes 13 and static magnetic device 28 such that the biotubes 13 and the static magnetic device 28 is suspended by static magnetic coil mounting rod 21 within the open interior space 62 of container 58 as more clearly shown in FIGS. 5 and 6.

Preferably, a computer system 24 is connected with the optical density reader device 32 where data collected by the laser beam passing through the biotubes 13 is manipulated and analyzed. Computer analysis includes a growth rate determination and, in a further aspect, the computer analysis includes transmission of a notice to a remote receiver (not shown for clarity) of a growth rate determination above a selected amount. The computer system 24 saves the data and then manipulates it by displaying it in graph form, for example only, such that the degree of increasing or decreasing cell activity (darker or lighter) is used to determine if there is a change in the growth rate of the organism in the biotube 13. Certainly, other types of data and other forms of data manipulation are included within the scope of the invention. For example only, in one aspect, the method further may also include a programmable computerized fluid sampling system connected to each biotube via micro-tubing that extracts minute quantities of liquids containing the studied microorganisms which is then systematically fed into a fluid imaging particle analyzer system (Fluid Imaging Technologies—Flow Cam analyzer) for additional in-depth study of the growth characteristics of each organism in the biostimulation research system.

ELEMENT LISTING AND DESCRIPTION

1 Electromagnetic biostimulation apparatus
2 outer wall of electromagnetic biostimulation apparatus which creates an inner wall of the container 58
3 inner reflective material on inner wall and on the bottom of the top 60 of container 58 to reflect light into the interior 62
4 holes through the apparatus through which the laser beam 6 passes to the optical density reader 32
5 laser beam device
6 path of optical density laser beam from laser beam device 5
7 rotating arm
8 direction of rotation of rotating arm
9 spacer for the biotube two tube (13 and 14) construction
10 humidifier/filter unit; preferably three units providing twelve sets of biotubes each with air
11 air adjustment valves
12 humidifier/filter service cap
13 biotube (outer tube)
14 inner air lift circulation tube located within biotube 13
15 air injection needle
16 metal magnetic shield if desired in some form
17 energy transmission device for containing microwave, or laser or acoustic EMF devices
18 electronic control box housing
19 recessed edge of top of apparatus
20 center rotating pole
21 static magnetic coil mounting rod
22 humidifier/filter drainage valve
23 microwave signal generator
24 computer/laptop system monitor
25 humidifier/filter water level
26 electronic control device
27 electrical conduit
28 static magnetic coil preferably 10 mT to 60 mT rare earth magnetic earth coil supported by mounting rod 21 in a preferred embodiment as illustrated
29 recessed edge of container top 60

30 horizontal adjustment for moving energy transmission device 17, EMF devices, microwave etc., left or right
31 light reflective thermo inner lining on all surfaces of the interior 62 of container 58 including the inside of the top 60 to reflect the light from the LED grow lights 44
32 laser optical density reader
33 vertical adjustment for moving energy transmission device 17, EMF devices, microwave etc., up or down
34 microwave, acoustic and/or laser energy radiating from energy transmission device 17
35 holes in center rotating pole for wiring
36 non-rotating lower base of apparatus
37 lowest open chamber of apparatus
38 casters for apparatus
39 band with laser holes 71 for allowing laser beam to pass through to laser optical density reader 32
40 power outlets on base of center rotating pole 20 for energy transmission device 17
41 air supply lines to biotubes 13
42 optical density laser beam power supply
43 one way check valve to prevent back-flow of water in the air supply lines 41
44 LED grow light preferably 45PCS*3 W—Pwer: 138 W—Input voltage 85-250V
45 main power switch
46 holes in inner air lift circulation tube 14 for water circulation
47 timer, preferably ENERLITES™ brand HET017-Day Digital In-wall Timer. Voltage: 120 VAC, 60 Hz, Resistive: 15Amp, 1800 W, Tungsten: 1200 W, Fluorescent: 1200 W, Motor: ½ Hp. This timer is programmable to control the regular light switch for energy-savings and security. It can be set to show the time as a clock. It can control incandescent lights, fluorescent lights, flood lights, stereos, of heavy-duty loads such as an air conditioner and motors.
48 LED power switch
49 air pump power switch
50 spare dimmer switch
51 spare electrical receptacle
52 rotor motor timer
53 energy transmission timer
54 LED timer
55 fan preferably a thermostatically controlled fan; preferably one thermo controlled AC fan for exhaust in top side and three thermo controlled AC fans in container bottom for air intake/cooling
56 fan switch
57 ventilation holes in bottom 59 of container 58
58 container
59 bottom of container
60 top of container; preferably top 60 is a removable machined ½" polypropylene table top of container with thirty-six 1¾" holes patterned to match the rotational angle of the laser optical density system beam as it rotates clockwise 360 degrees
61 top edge of container
62 open interior space of container
63 microwave EMF device
64 acoustic EMF device
65 EMF device, preferably laser generated
66 first end of support arm 7
67 second end of support arm 7
68 adjustable middle of support arm 7
69 test biotubes
70 control biotubes
71 laser beam holes
72 air pump
73 AC catalytic, thermo controlled, heater for maintaining optimal temperature settings for bio-organism growth conditions in the upper growth container area of the biotubes.

Figure 3:
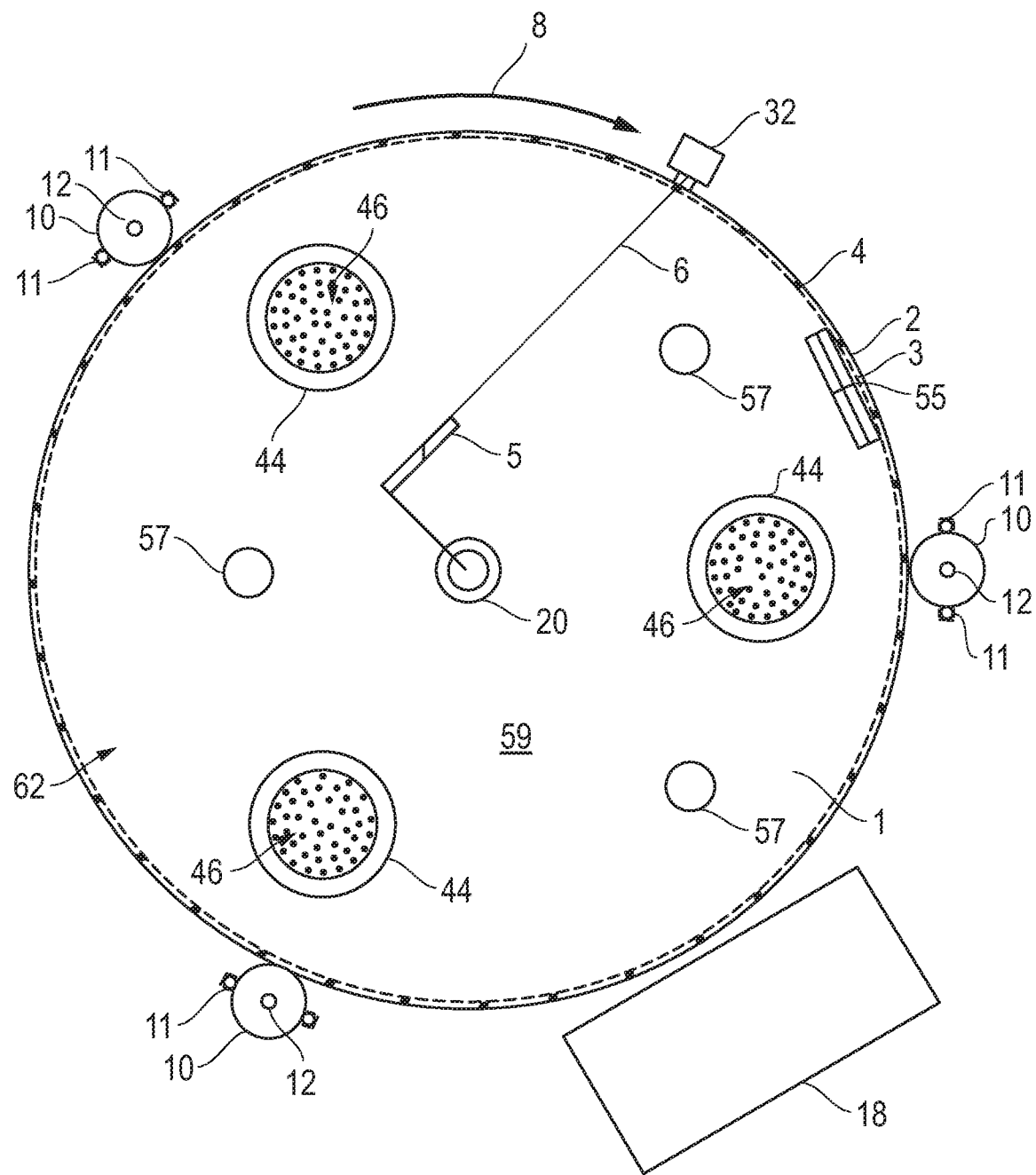
FIG. 3 is a top inside view of the invention of FIG. 1 illustrating other elements.

By way of continued explanation and referring to the descriptive elements listed above, FIG. 3 is a top inside view of the invention of FIG. 1 illustrating other elements including three LED grow lights 44 preferably located in the bottom 59 of container 28 such that light from the LED grow lights is projected upward and over all the biotubes 13, both test biotubes 69 and control biotubes 70. Ventilation holes 57 in the bottom 59 of container 58 are preferably provided as well.

Figure 4:
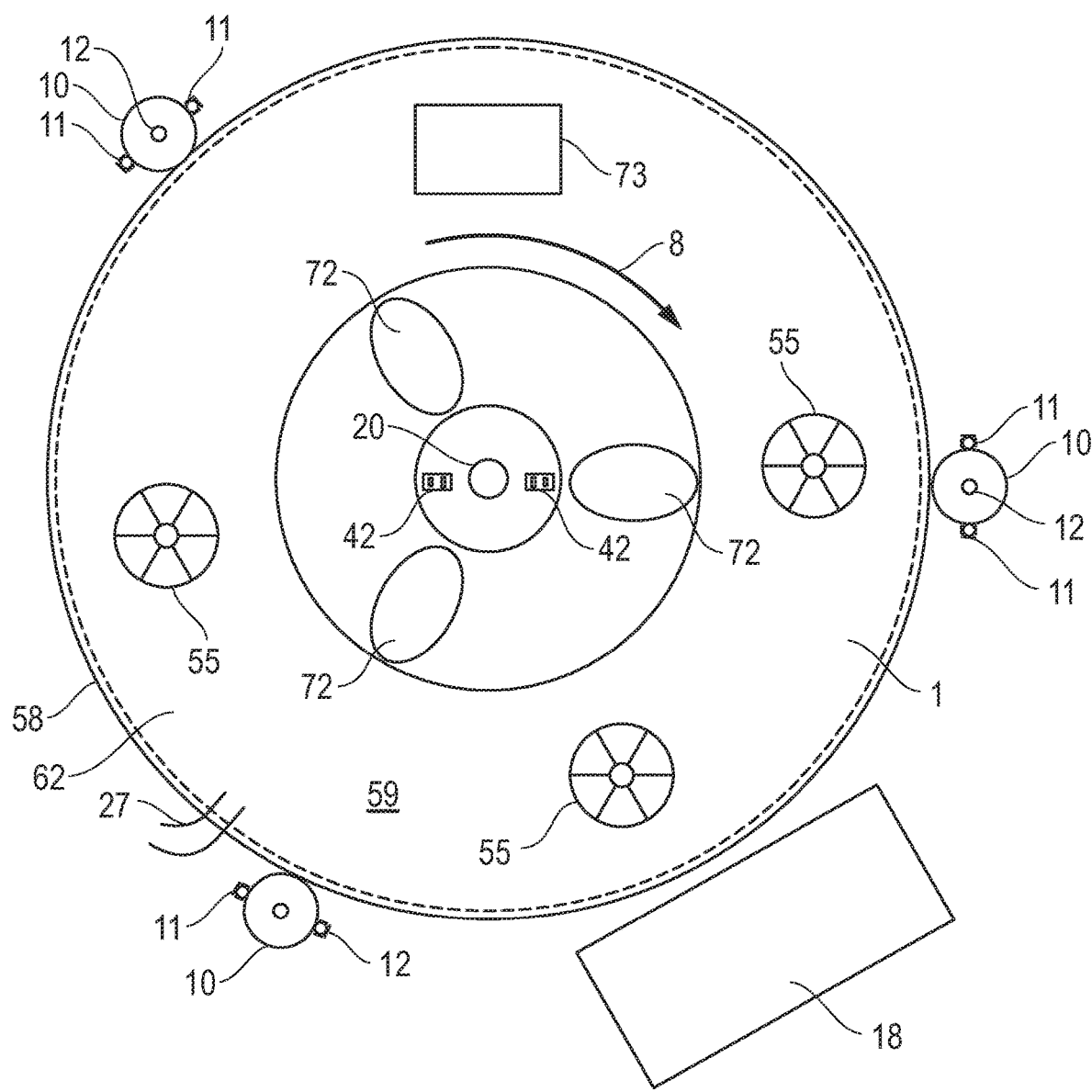
FIG. 4 is a top inside bottom view of the invention of FIG. 1.

FIG. 4 is a top inside bottom view of the invention of FIG. 1 showing the preferred arrangement of air pump 72. Preferably three air pumps 72 are provided and send air to the air humidifiers 10 as illustrated more clearly in FIG. 5. FIG. 4 also illustrates a preferred embodiment including three thermo controlled AC fans 55 in container 58 bottom 59 for air intake/cooling. Also illustrated is a preferred AC catalytic, thermo controlled, heater 73 for maintaining optimal temperature settings for bio-organism growth conditions in the upper growth container area of the biotubes.

FIG. 5 is a side partial cut away view of the invention of FIG. 1 and clearly illustrates the location and structure of each of the above described elements of the invention.

FIG. 6 is a side partial cut away view of the invention of FIG. 1 illustrating other elements such as electronic control device 26 and, again, a thermostatically controlled fan 55 near the top 60 of container 58 for user controlled temperature regulation assistance.

Figure 7:
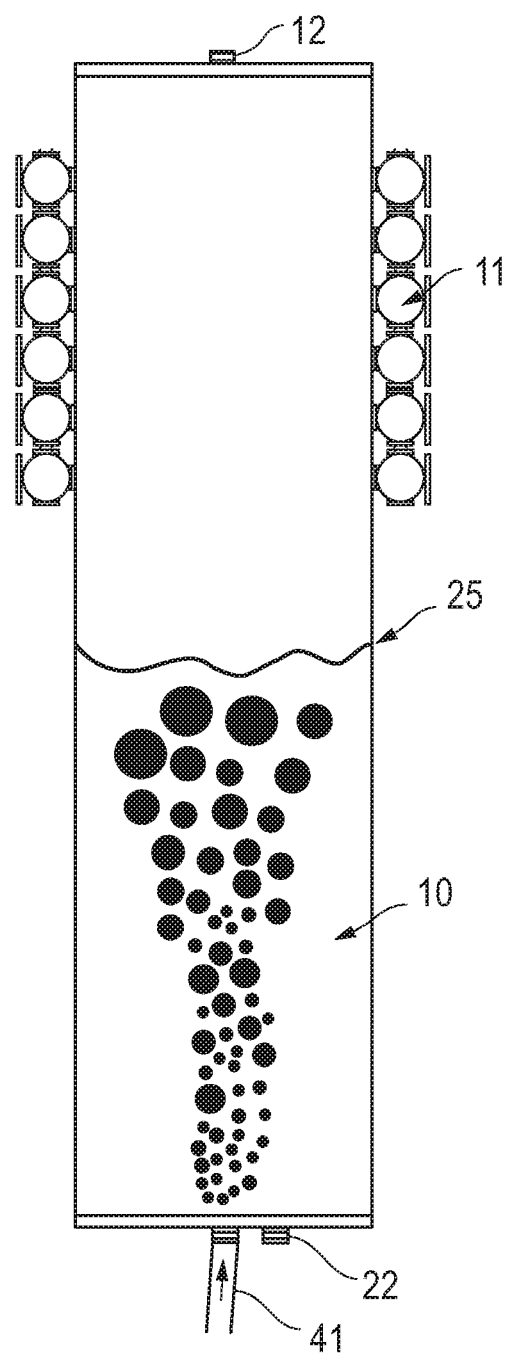
FIG. 7 is a close up side view of the air filter-humidifier of the invention of FIG. 1.

FIG. 7 is a close up side view of a preferred embodiment of the air filter-humidifier 10 of the invention of FIG. 1 and associated structural elements as disclosed herein.

Figure 8:
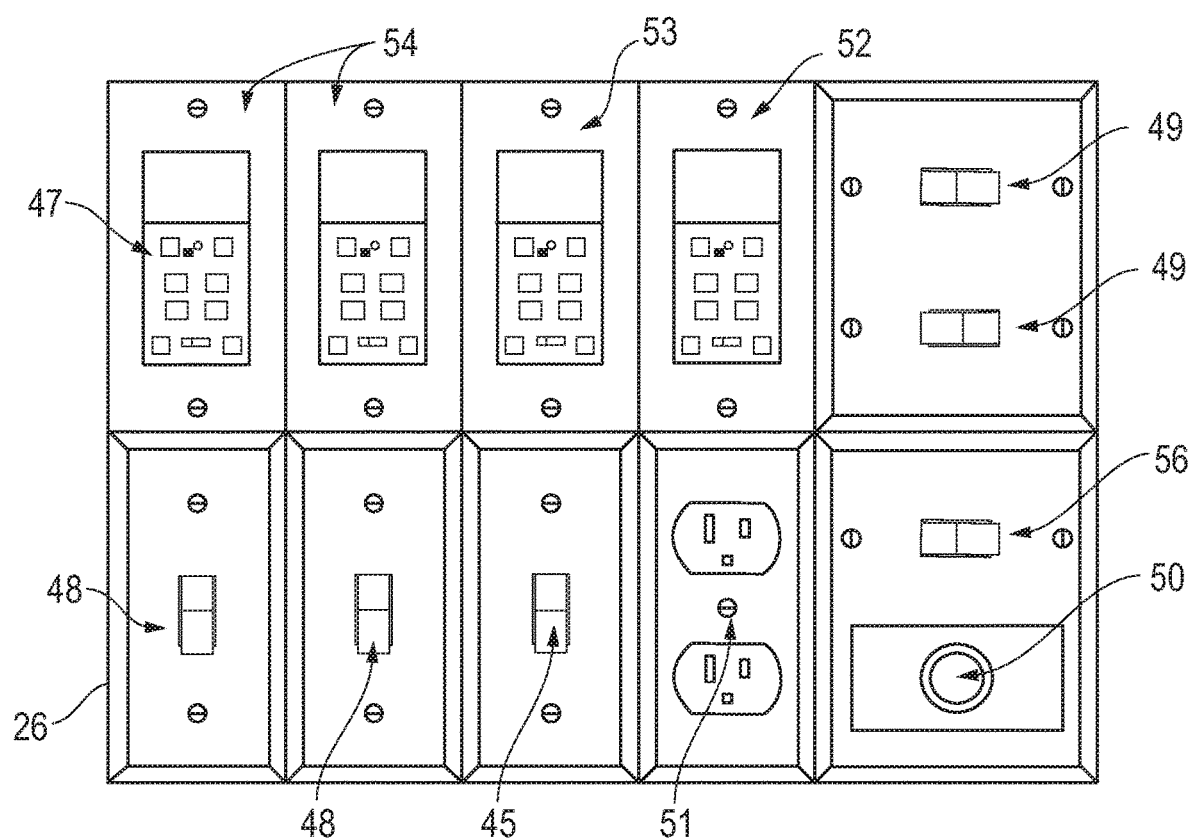
FIG. 8 is a front view of the electrical control box of the invention of FIG. 1.

FIG. 8 is a front view of the electronic control device 26 including a preferred embodiment assembly of operational control switches as identified and described herein.

Figure 9:
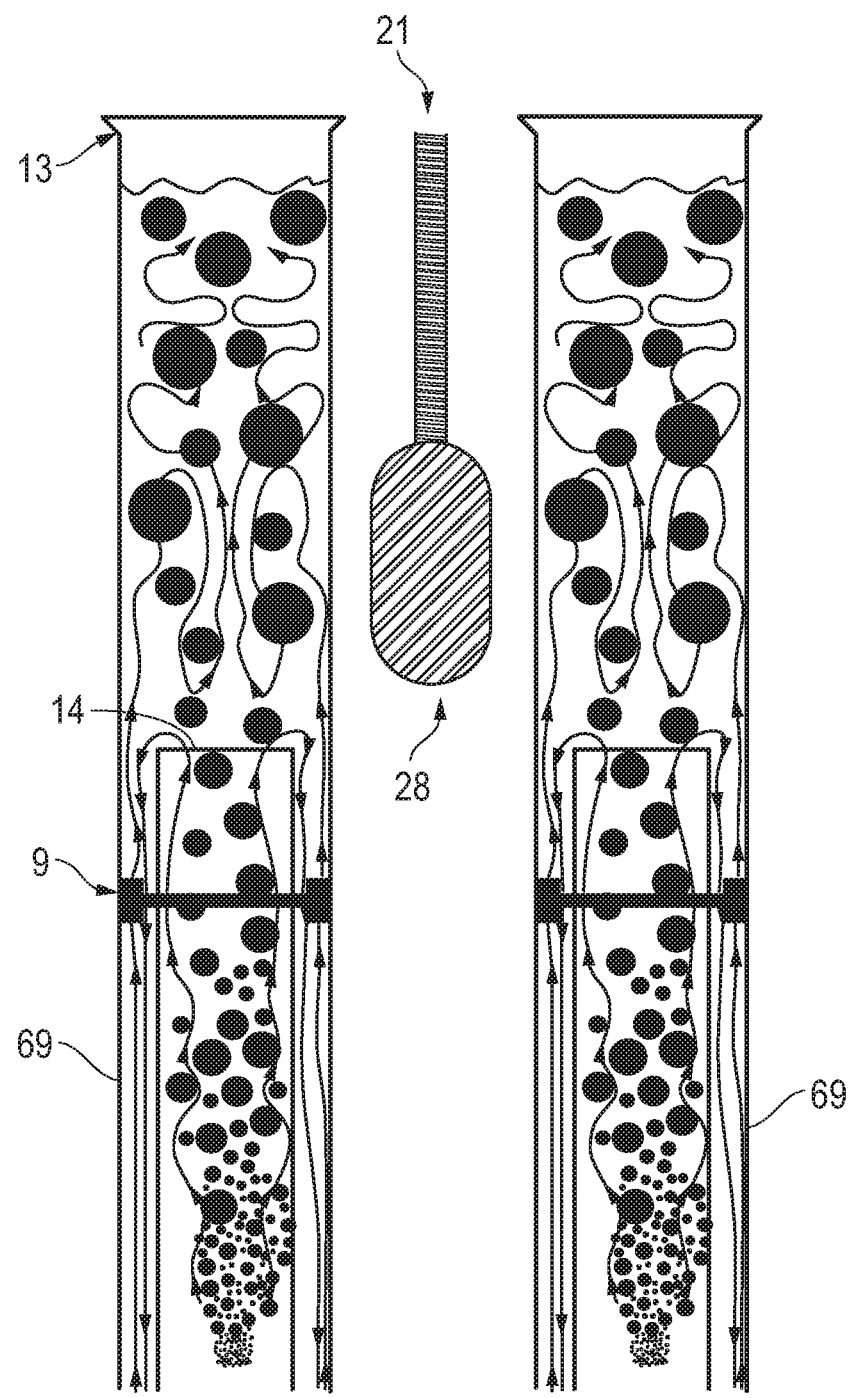

FIG. 9 is a side close up view of two test biotubes 69 of the invention of FIG. 1 with a static magnetic coil 28 in between.

Figure 10:
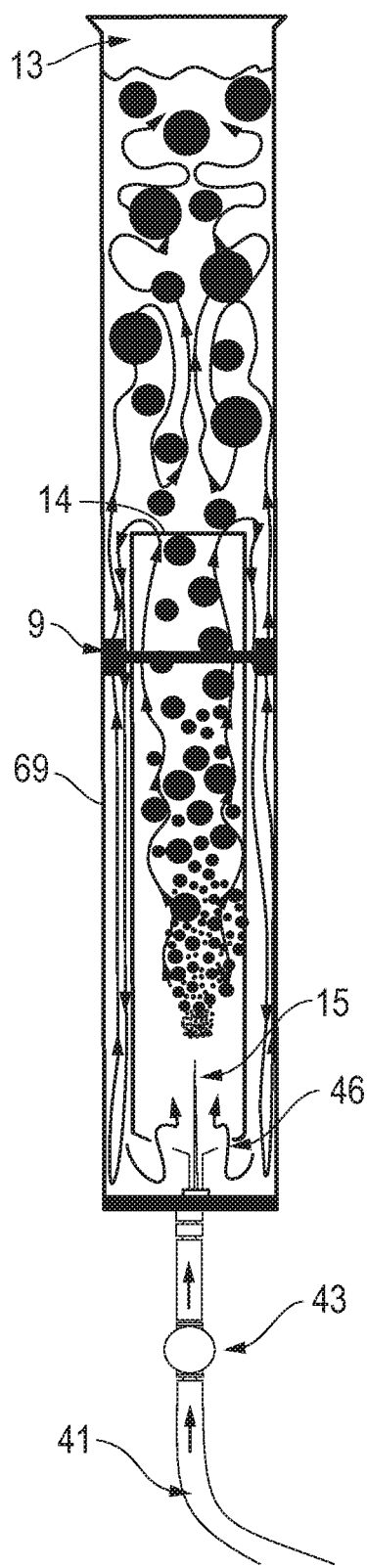
FIG. 10 is a side close up view of the biotube of the invention of FIG. 1.

FIG. 10 is a side close up view of the biotube 13 of the invention of FIG. 1 along with associated structural elements as described herein.

The description of the present embodiments of the invention has been for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. An electromagnetic biostimulation apparatus comprising:
   a. a circular container with an outer wall, a bottom, and a top with a top edge such that an open interior space is formed;
   b. a plurality of biotubes located in misaligned concentric rings within said circular container wherein said plurality of biotubes includes test biotubes and control biotubes;
   c. a rotating center pole located at the center of said circular container open interior space and extending above said circular container wherein said rotating center pole includes a transverse support arm with a first end, a second end and a middle wherein the middle of the transverse support arm is connected with the rotating center pole above the circular container;

c. a microwave emitter, an acoustic emitter and a laser electromagnetic field (EMF) energy emitter connected to the first end of said transverse support arm such that the microwave emitter, acoustic emitter and a laser electromagnetic field (EMF) energy emitter rotate above the test biotubes;

d. a laser beam emitter connected to the rotating center pole and an optical density reader connected to the second end of said transverse support arm such that the optical density reader rotates around the outside of said circular container;

e. a static magnet located within said circular container and in proximity to said test biotubes; and d. a hole in said circular container wherein said optical density reader obtains data from said laser beam related to each of said plurality of biotubes.

2. The apparatus of claim 1 wherein the test biotubes are located between the rotating center pole and the control tubes and the control tubes are located in proximity to the outer wall.

3. The apparatus of claim 2 wherein the biotubes form three misaligned concentric rings around the rotating center pole with test biotubes in two of the misaligned concentric rings.

4. The apparatus of claim 3 wherein there are a total of thirty-six biotubes with twelve test biotubes in two of the misaligned concentric rings and twelve control biotubes in the third misaligned concentric ring.

5. The apparatus of claim 1 further including a plurality of laser beam holes in the outer edge of the circular container wherein the laser beam holes are configured such that a laser beam passes through each of the plurality of biotubes as it rotates and through a laser beam hole to the optical density reader for data collection for each of said test biotubes and each of said control biotubes.

6. The apparatus of claim 1 further including a computer system connected with the optical density reader wherein data from said plurality of biotubes is manipulated and analyzed.

7. The apparatus of claim 6 wherein said computer analysis includes a growth rate determination.

8. The apparatus of claim 7 wherein said computer analysis includes transmission of a notice to a remote receiver of a growth rate determination above a selected amount.

* * * * *